(12) United States Patent
Krishnan et al.

(10) Patent No.: US 11,101,043 B2
(45) Date of Patent: Aug. 24, 2021

(54) HYBRID ANALYSIS FRAMEWORK FOR PREDICTION OF OUTCOMES IN CLINICAL TRIALS

(71) Applicant: Zasti Inc., Oakton, VA (US)

(72) Inventors: Ramanathan Krishnan, Oakton, VA (US); John Domenech, Big Pine Key, FL (US); Rajagopal Jagannathan, Chennai (IN); Sharath Makki Shankaranarayana, Chennai (IN)

(73) Assignee: Zasti Inc., Oakton, VA (US)

( * ) Notice: Subject to any disclaimer, the term of this patent is extended or adjusted under 35 U.S.C. 154(b) by 0 days.

(21) Appl. No.: 16/578,980

(22) Filed: Sep. 23, 2019

(65) Prior Publication Data

US 2020/0098451 A1  Mar. 26, 2020

Related U.S. Application Data

(60) Provisional application No. 62/735,703, filed on Sep. 24, 2018.

(51) Int. Cl.
| | | |
|---|---|---|
| *G16H 50/50* | (2018.01) | |
| *G06N 3/08* | (2006.01) | |
| *G16H 10/20* | (2018.01) | |
| *G06N 20/20* | (2019.01) | |
| *G16H 50/70* | (2018.01) | |
| *G16H 50/20* | (2018.01) | |
| *G06N 3/04* | (2006.01) | |

(52) U.S. Cl.
CPC ............... *G16H 50/50* (2018.01); *G06N 3/08* (2013.01); *G06N 20/20* (2019.01); *G16H 10/20* (2018.01); *G16H 50/20* (2018.01); *G16H 50/70* (2018.01); *G06N 3/0445* (2013.01); *G06N 3/0454* (2013.01)

(58) Field of Classification Search
CPC ........ G16H 10/20; G16H 50/70; G16H 50/20; G16H 50/50; G06N 3/08; G06N 3/0445; G06N 3/0454; G06N 20/20
See application file for complete search history.

(56) References Cited

U.S. PATENT DOCUMENTS

| | | |
|---|---|---|
| 9,536,194 B2 | 1/2017 | Cao et al. |
| 9,754,220 B1 | 9/2017 | Brestoff et al. |
| 10,327,709 B2 * | 6/2019 | Heldt .................... G16H 50/70 |

(Continued)

FOREIGN PATENT DOCUMENTS

| | | |
|---|---|---|
| CN | 107133481 A | 9/2017 |
| WO | 2014/137892 A1 | 9/2014 |

OTHER PUBLICATIONS

Hothorn et al., Survival ensembles, Dec. 12, 2005, Biostatistics, pp. 355-373. (Year: 2005).*

(Continued)

*Primary Examiner* — Christopher L Gilligan
(74) *Attorney, Agent, or Firm* — Seed IP Law Group LLP

(57) ABSTRACT

A facility for predicting patient outcomes on the basis of clinical trials is described. The facility obtains information describing one or more completed clinical trials, and extracts features from the obtained clinical trial information. The facility uses the extracted features to train both a time-series data model for predicting clinical outcomes and a non-time-series data model for predicting clinical outcomes. The facility applies these trained models to information describing a subject patient to predict a clinical outcome for the subject patient.

18 Claims, 12 Drawing Sheets

(56) References Cited

U.S. PATENT DOCUMENTS

| | | | |
|---|---|---|---|
| 2004/0101181 A1 | 5/2004 | Giger et al. | |
| 2007/0105136 A1 | 5/2007 | Staudt et al. | |
| 2007/0248948 A1 | 10/2007 | Hatzis et al. | |
| 2008/0033894 A1* | 2/2008 | Steck | G06F 19/00 706/12 |
| 2009/0234627 A1 | 9/2009 | Yu et al. | |
| 2010/0057651 A1 | 3/2010 | Fung et al. | |
| 2012/0269418 A1 | 10/2012 | McCulloch et al. | |
| 2013/0116511 A1 | 5/2013 | Sui | |
| 2013/0262357 A1 | 10/2013 | Amarasingham et al. | |
| 2014/0279754 A1 | 9/2014 | Barsoum et al. | |
| 2016/0140442 A1 | 5/2016 | Lee et al. | |
| 2016/0283679 A1 | 9/2016 | Hu et al. | |
| 2016/0328526 A1* | 11/2016 | Park | G06N 20/00 |
| 2017/0323063 A1 | 11/2017 | Krause et al. | |
| 2017/0357760 A1 | 12/2017 | Han et al. | |
| 2018/0018757 A1 | 1/2018 | Suzuki | |
| 2018/0107791 A1 | 4/2018 | Guo et al. | |
| 2018/0158552 A1* | 6/2018 | Liu | G16H 50/70 |
| 2018/0348235 A1 | 12/2018 | Vigue et al. | |
| 2019/0378619 A1* | 12/2019 | Meyer | G16H 50/70 |

OTHER PUBLICATIONS

Watt, Exploring Temporal Frameworks for Constructing Longitudinal Instance-Specific Models from Clinical Data, 2012, UMI ProQuest, pp. 1-238. (Year: 2012).*

Zhang, Mining Clinical Data for Trauma Patients, Sep. 2016, ProQuest, pp. 1-108. (Year: 2016).*

* cited by examiner

US 11,101,043 B2

HYBRID ANALYSIS FRAMEWORK FOR PREDICTION OF OUTCOMES IN CLINICAL TRIALS

CROSS-REFERENCE TO RELATED APPLICATIONS

This Application claims the benefit of provisional U.S. Application No. 62/735,703, filed Sep. 24, 2018 and entitled "TIME SERIES ANALYSIS FRAMEWORK FOR PREDICTION OF KEY OUTCOMES IN CLINICAL TRIALS," which is hereby incorporated by reference in its entirety.

In cases where the present application conflicts with a document incorporated by reference, the present application controls.

BACKGROUND

Cancer is a heterogeneous disease having many different subtypes. Cancer rates worldwide are consistently on the rise, and many cancer types and subtypes can become life-threatening.

DETAILED DESCRIPTION

Figure 1:
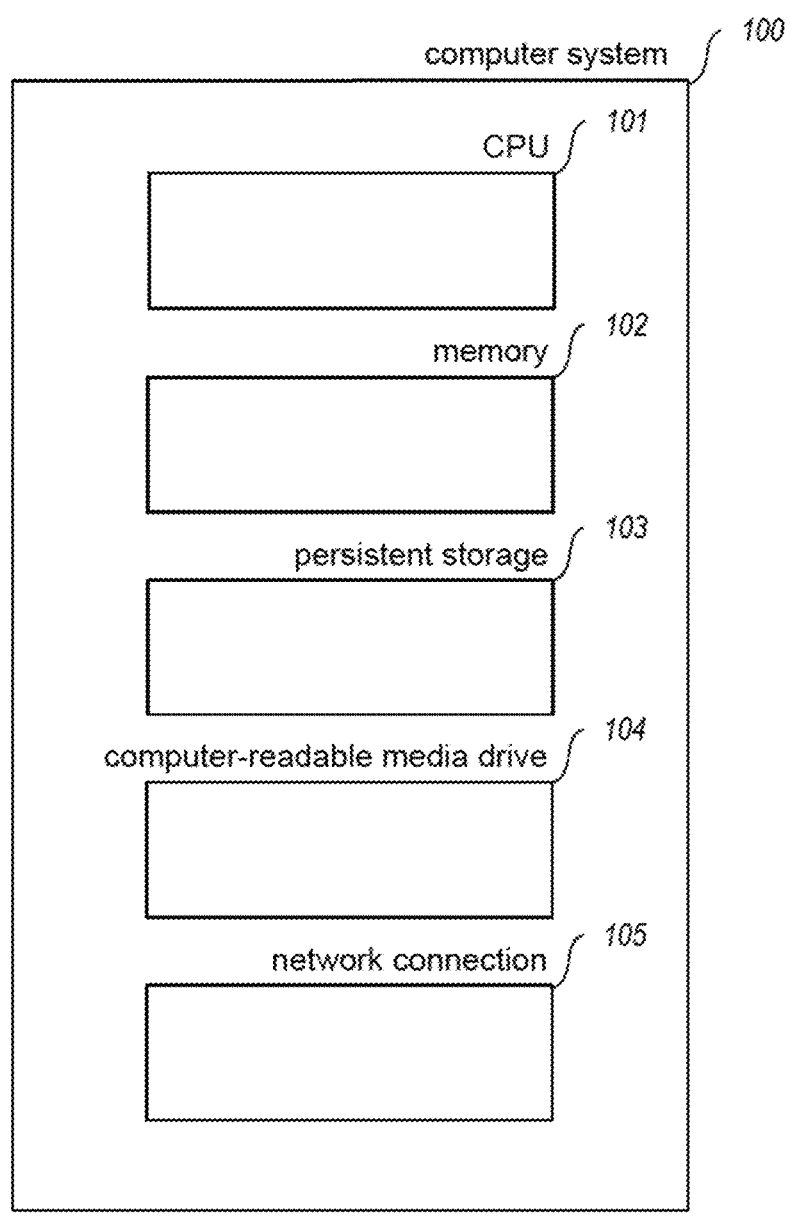
FIG. 1 is a block diagram showing some of the components typically incorporated in at least some of the computer systems and other devices on which the facility operates.

The inventors have recognized the value of performing three predictive tasks in managing cancer patients: (i) predicting cancer susceptibility (risk assessment), (ii) predicting cancer recurrence/local control and (iii) predicting cancer survival. In the first two cases, one is trying to find (1) the likelihood of developing a type of cancer, and (2) the likelihood of redeveloping a type of cancer after complete or partial remission. In the last case, the prediction of a survival outcome such as disease-specific or overall survival after cancer diagnosis or treatment is the main objective. The prediction of cancer outcome usually refers to predicting one or more of (a) life expectancy, (b) survivability, (c) progression, and (d) treatment sensitivity.

In response, the inventors have conceived and reduced to practice a software and/or hardware facility that uses a hybrid learning-based framework to perform data-mining and analysis of time series health care data ("the facility"). As an initial step, the facility mines and extracts relevant data specific to the task at hand and performs feature engineering by utilizing domain knowledge. The facility uses the extracted data to build machine learning models to predict outcomes of interest. Since health care data often includes longitudinal or time-series information, in some embodiments the facility builds deep learning models that utilize the time-series nature of the health care data and are thus capable of refining the predictions sequentially in accordance with the time series data. The facility can analyze cancer clinical trials to provide personalized predictions for patients in various domains.

In some embodiments, the facility uses a time series analysis framework to predict key outcomes in clinical trials, such as overall survival of a patient, disease-free progression survival of a patient, probability of adverse events, etc. In some embodiments, the facility pursues a methodology for data-driven patient grouping across trials into multiple categories, analysis of similarities in presentation and response and suggestions for informative parameters. This helps the clinicians by providing informative cues and also serves as a tool for the trialists to perform patient matching. In some embodiments, the facility generates a dashboard that enables caregivers to continuously monitor early response, anticipatory treatment based on predicted adverse reactions and predicted response and planning treatment durations, described further below in connection with FIGS. 5-12.

In some embodiments, the facility first analyzes the data to identify prognostic factors, then the facility models the relationship between the prognostic factors and observed patient survival.

In various embodiments, the facility uses clinical trial data of a variety of types to extract domain specific features and produce informative report on the clinical trial.

By performing in some or all of these ways, the facility provides insights into clinical trials, and uses the data they produce to predict treatment efficacy in other patients.

FIG. 1 is a block diagram showing some of the components typically incorporated in at least some of the computer systems and other devices on which the facility operates. In various embodiments, these computer systems and other devices 100 can include server computer systems, cloud computing platforms or virtual machines in other configurations, desktop computer systems, laptop computer systems, netbooks, mobile phones, personal digital assistants, televisions, cameras, automobile computers, electronic media players, etc. In various embodiments, the computer systems and devices include zero or more of each of the following: a central processing unit ("CPU") 101 for executing computer programs; a computer memory 102 for storing programs and data while they are being used, including the facility and associated data, an operating system including a kernel, and device drivers; a persistent storage device 103, such as a hard drive or flash drive for persistently storing programs and data; a computer-readable media drive 104, such as a floppy, CD-ROM, or DVD drive, for reading programs and data stored on a computer-readable medium; and a network connection 105 for connecting the computer system to other computer systems to send and/or receive data, such as via the Internet or another network and its networking hardware, such as switches, routers, repeaters, electrical cables and optical fibers, light emitters and receivers, radio transmitters and receivers, and the like. While computer systems configured as described above are typically used to support the operation of the facility, those skilled in the art will appreciate that the facility may be implemented using devices of various types and configurations, and having various components.

Figure 2:
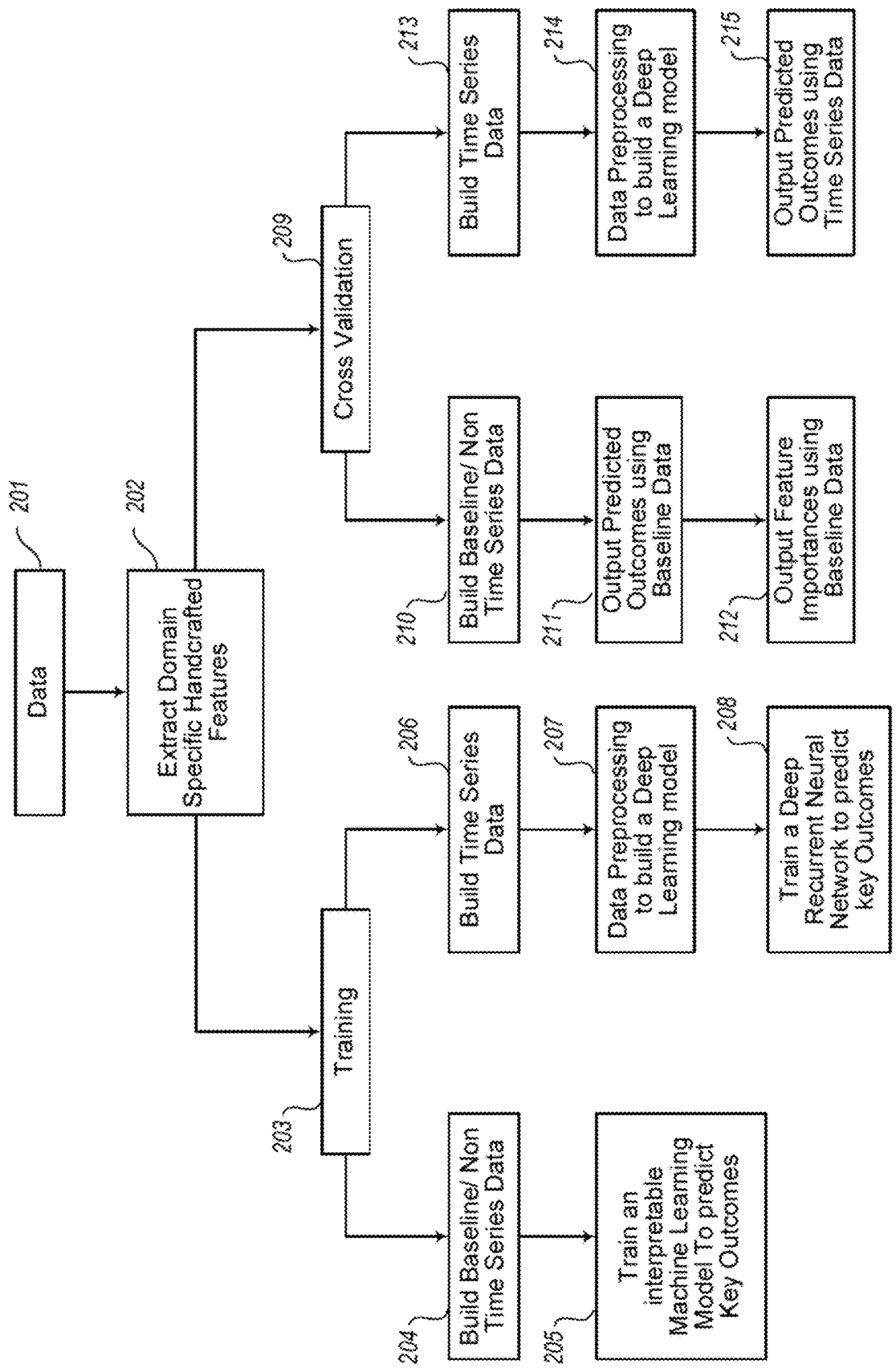
FIG. 2 is a flowchart showing a process performed by the facility in some embodiments to train, apply, and validate a model for predicting medical outcomes for patients based upon clinical trial outcomes and associated patient data features.

FIG. 2 is a flowchart showing a process performed by the facility in some embodiments to train, apply, and validate a model for predicting medical outcomes for patients based upon clinical trial outcomes and associated patient data features. The facility begins with patient data 201 including, for each patient, dependent variable values, time-series independent variable values, and non-time series independent variable values. In act 202, the facility mines digital records and performs feature engineering needed for the task. The facility performs this feature engineering with the knowledge of the domain at hand. In act 202, the facility also splits the data into training 203 and validation 209 data sets, in some embodiments observing standard conventions for performing ten-fold cross validation. In some embodiments, the facility trains and applies together two kinds of learning-based submodels: (1) an interpretable machine learning submodel for the baseline/non time-series data, and (2) a deep learning submodel for the time-series data. In act 203, the facility initiates training of both of these two sub models.

In some embodiments, the facility uses gradient boosted trees as the interpretable machine learning model to train and predict an outcome of interest, such as predicting the likelihoods of overall survival or progression free survival or adverse effects, etc., in the case of cancer trials. The model takes in only baseline or non-time series data, and thus serves as a baseline predictor. The interpretable machine learning model also provides a list of features influencing the decision, enabling clinicians to gain insights on the cancer trials.

Gradient boosting is a machine learning technique for regression and classification problems that produces a prediction model in the form of an ensemble of weak prediction models, such as decision trees. The facility builds the model in a stage-wise fashion, and it generalizes other boosting methods by allowing optimization of an arbitrary differentiable loss function.

Gradient boosting involves three elements: (a) A loss function to be optimized, (b) a weak learner to make predictions, and (c) an additive model to add weak learners. Some advantages of applying gradient boosted trees to this problem are: natural handling of data of mixed type (i.e., heterogeneous features); predictive power; and robustness to outliers in output space.

The facility's use of gradient boosting often produces an excellent fit of the predicted values to the observed values, even where the specific nature of the relationships between the predictor variables and the dependent variable of interest is very complex (nonlinear in nature). Thus, gradient boosted trees, which involve fitting a weighted additive expansion of simple trees, represents a very powerful machine learning algorithm.

In act 204, the facility constructs the gradient boosting interpretable machine learning model for baseline/non-time series data. In act 205, the facility uses the dependent variable values and independent non-time series variable values in the training observations to train the interpretable machine learning model constructed in act 204.

For the second kind of learning model, in some embodiments the facility uses a recurrent neural network based deep learning algorithm for prediction. A recurrent neural network is a type of neural network that is capable of handling sequential data.

Figure 3:
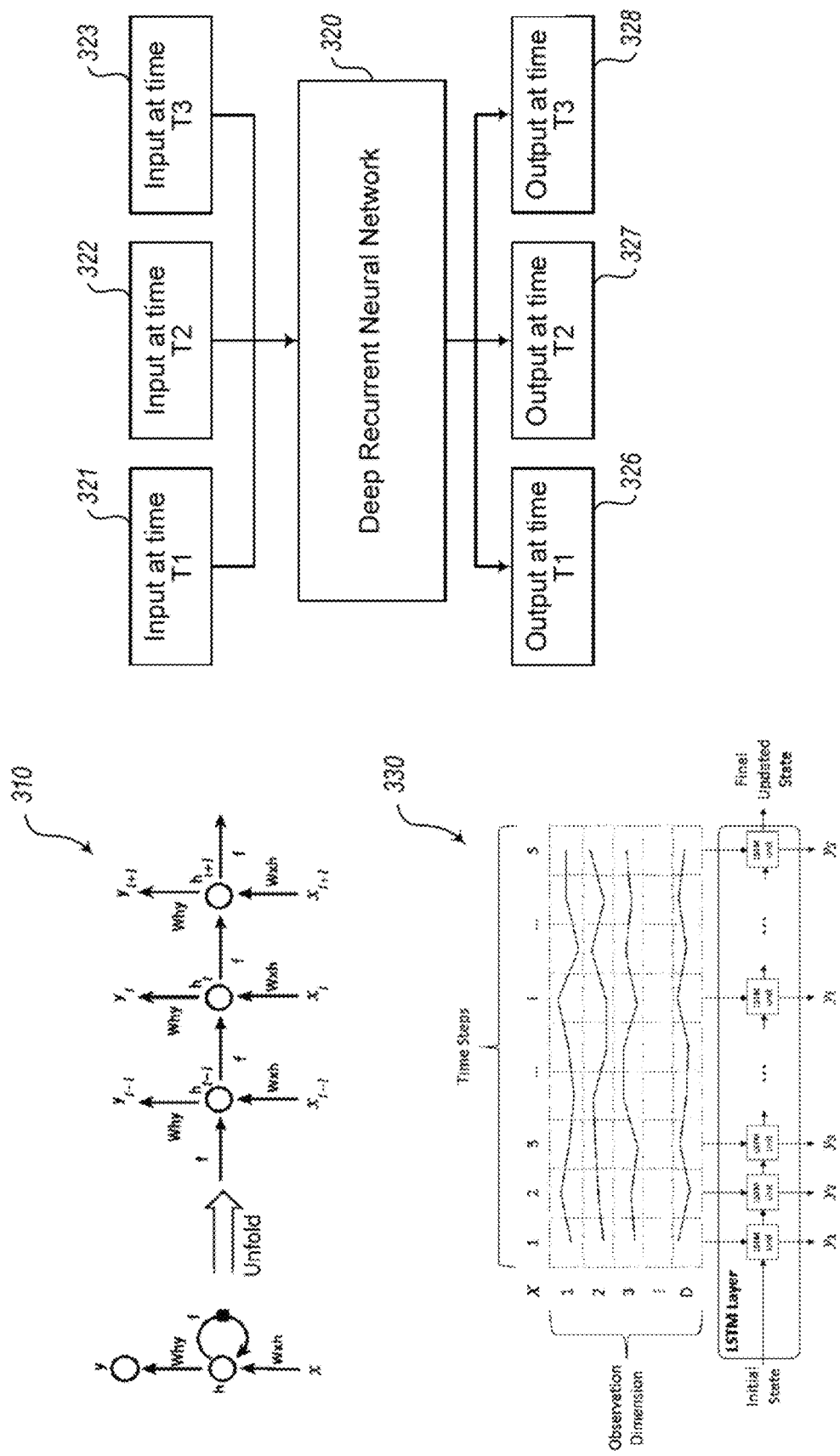
FIG. 3 is a model diagram visually portraying versions of the deep learning model used by the facility for time series data in some embodiments.

FIG. 3 is a model diagram visually portraying versions of the deep learning model used by the facility for time series data in some embodiments. As shown in illustration 310, the recurrent neural networks used by the facility in some embodiments are artificial neural networks where the computation graph contains directed cycles. Unlike feedforward neural networks in which information flows strictly in one direction from layer to layer, in recurrent neural networks (RNNs), information travels in loops from layer to layer so that the present state of the model is influenced by its previous states. While feedforward neural networks can be thought of as stateless, RNNs have a memory that allows the model to store information about its past computations. This in turn allows recurrent neural networks to exhibit dynamic temporal behavior and model sequences of input-output pairs, as shown in illustration 320, generating different outputs 326-328 at different times in response to different inputs 321-323 at the corresponding times. In some embodiments, each output at a particular time reflects the input at that time and all earlier times. For example, the output 328 at time $T_3$ reflects the inputs 321-323 at times $T_1$-$T_3$. Because they can model temporal sequences of input-output pairs, recurrent neural networks have found enormous success in natural language processing (NLP) and time-series applications. However, there exists an issue with some conventional uses of RNNs known as the vanishing/exploding gradients problem: for long input-output sequences, RNNs often have trouble modelling long-term dependencies between elements in the sequence that are separated by large periods of time. In some embodiments, the system uses RNN variants such as LSTMs (Long Short-Term Memory) as shown in illustration 330 that are capable of overcoming the vanishing/exploding gradient problem, enabling RNNs to be safely be applied to extremely long sequences, even ones that contain millions of elements.

Since, for the case of clinical trials, patients undergo tests at regular intervals, there is a natural availability of time series data. The facility employs the specific type of recurrent neural network (RNN) called the long short-term memory (LSTM) for the task of predicting the key outcomes like overall survival and progression free survival. The advantage of using LSTMs over baseline learning models is that the LSTMs handle the time-series nature of the data and refine the predictions upon receiving additional time series data, which the baseline models are incapable of performing. This also helps the clinicians or trialists to sequentially monitor the progress of the patient and make necessary changes in between the treatment to aid the patient in their recovery.

Returning to FIG. 2, in act 206, the facility constructs its time series data model. In act 207, the facility performs data preprocessing as a basis for training the deep learning model for time series data constructed in act 206. In act 208, the facility uses the preprocessed dependent variable values and time series independent variable values from the training observations to train the deep learning model for time series data, such as a deep recurrent neural network, to predict patient outcomes.

As discussed below, the facility uses the cross validation data 209 reserved from data 201 to perform validation of the models trained in acts 205 and 208. In particular: In act 210, the facility builds baseline/non-time series data. In act 211, the facility outputs predicted outcomes using this baseline data. In act 212, the facility outputs feature importance indications using this baseline data. Additionally, in act 213, the facility builds time series data. In act 214, the facility performs data preprocessing to build a deep learning model. In act 215, the outputs predicted outcomes using the time series data.

After the facility trains and tests its two sub models, it uses them to predict outcomes for particular patients on the basis of their time series and non-time series independent variable values, and joins their predictions into one overall prediction for each patient.

Figure 4:
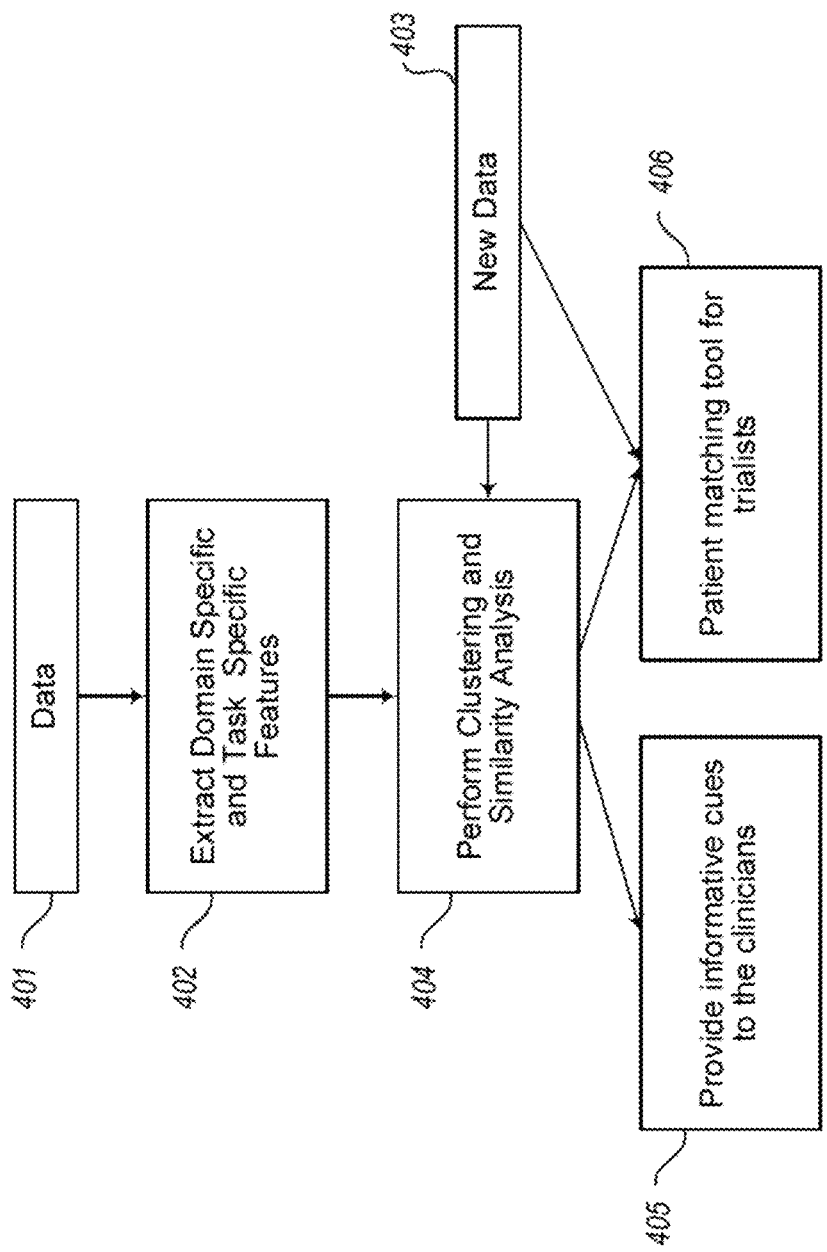
FIG. 4 is a flow diagram showing a process performed by the facility in some embodiments to perform data-driven patient grouping across trials into multiple categories as a basis for populating these trials with patients.

FIG. 4 is a flow diagram showing a process performed by the facility in some embodiments to perform data-driven patient grouping across trials into multiple categories as a basis for populating these trials with patients. The facility begins in act 401 with patient data. In act 402, the facility extracts domain-specific and task-specific features from the data. In act 403, the facility acquires new data. In act 404, the facility performs clustering and similarity analysis on the basis of the new data, and the extracted features. In act 405, the facility uses the analysis performed in act 404 to provide informative cues to clinicians. In act 406, the facility uses the analysis performed in act 404 to perform the matching of particular patients with particular trials.

In some embodiments, the described learning-based time series analysis facility is integrated with electronic health record logging system. The electronic health record consists of individual patients' information, and is updated by the clinicians or trialists on an ongoing basis. The facility directly predicts key outputs such as overall survival of the patient and progression free survival of the patient and other informative predictions of interests to the clinicians or trialists. In various embodiments, the facility performs predictions on a standalone computer or a cloud computing architecture.

In some embodiments, the facility operates in a teleconsulting mode where the learning framework need not reside at the site of trial of clinic which logs in the patient electronic health record data; rather, the electronic health record data is transmitted over internet to a remote computer hosting the learning framework in the prediction mode. The report is prepared remotely and can be proof-read at a third remote location. The final report can be relayed back to the clinicians or trialists.

In various embodiments, the facility performs various other kinds of predictive modelling tasks, such as prediction of failure time of components, which is an important predictive task in the industry sector; prediction or modelling of airplane delays in the aircraft sector; etc.

In various embodiments, the facility provides a variety of visual user interfaces that assist clinicians and others to obtain information about clinical trials and predictions made from them by the facility.

Figure 5:
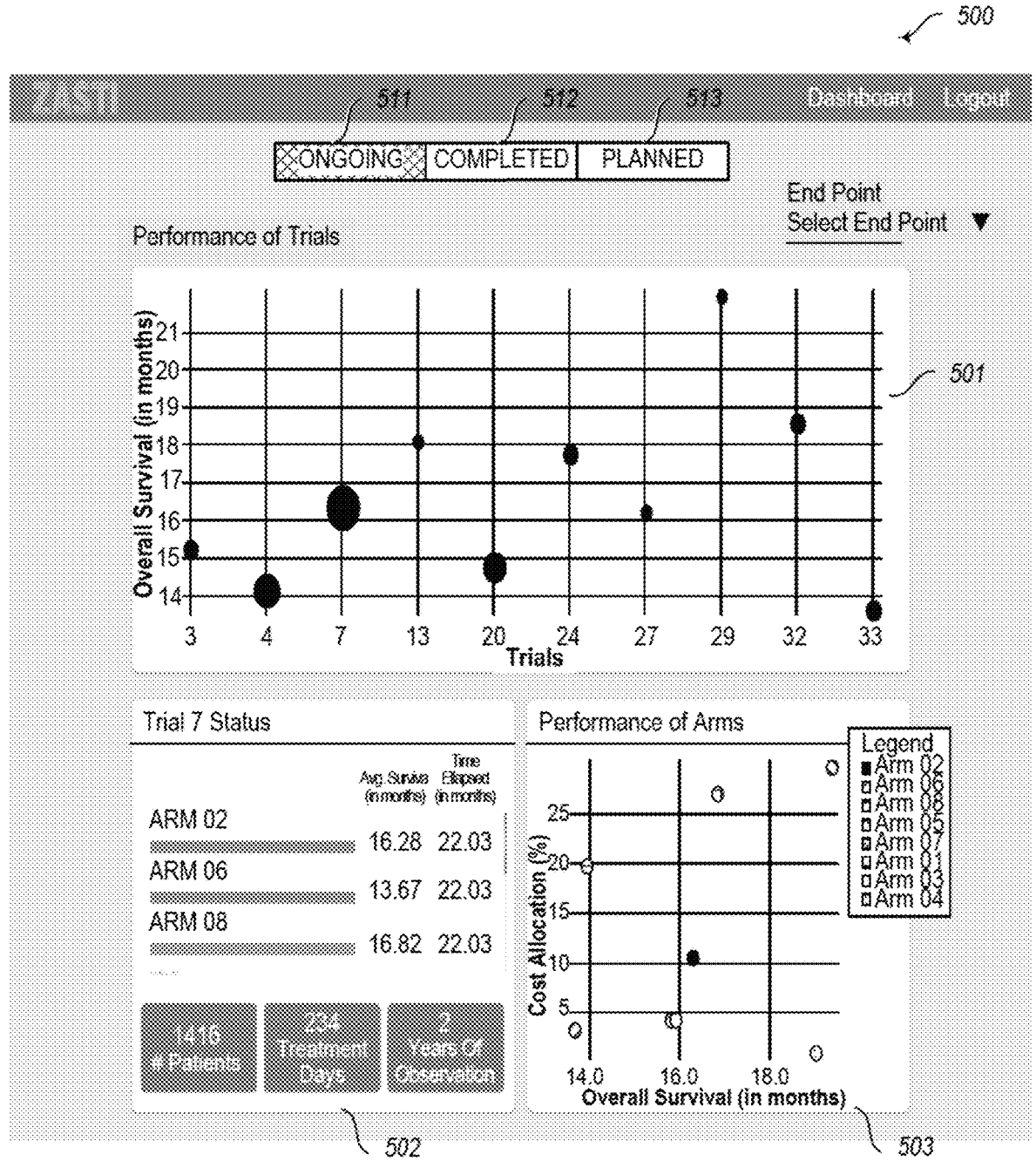
FIG. 5 is a display diagram showing a customizable clinical trials dashboard presented by the facility in some embodiments.

FIG. 5 is a display diagram showing a customizable clinical trials dashboard presented by the facility in some embodiments. The dashboard 500 contains charts 501, 502 and 503 each showing information about an overall survival rate metric. In various embodiments, the facility presents similar dashboards for a variety of other outcome metrics, including progression-free survival, adverse reaction, and others. The dashboard also includes controls for 511-513 that the user can select in order to show information in the displayed charts relating to ongoing trials, completed trials and planned trials, respectively.

Figure 6:
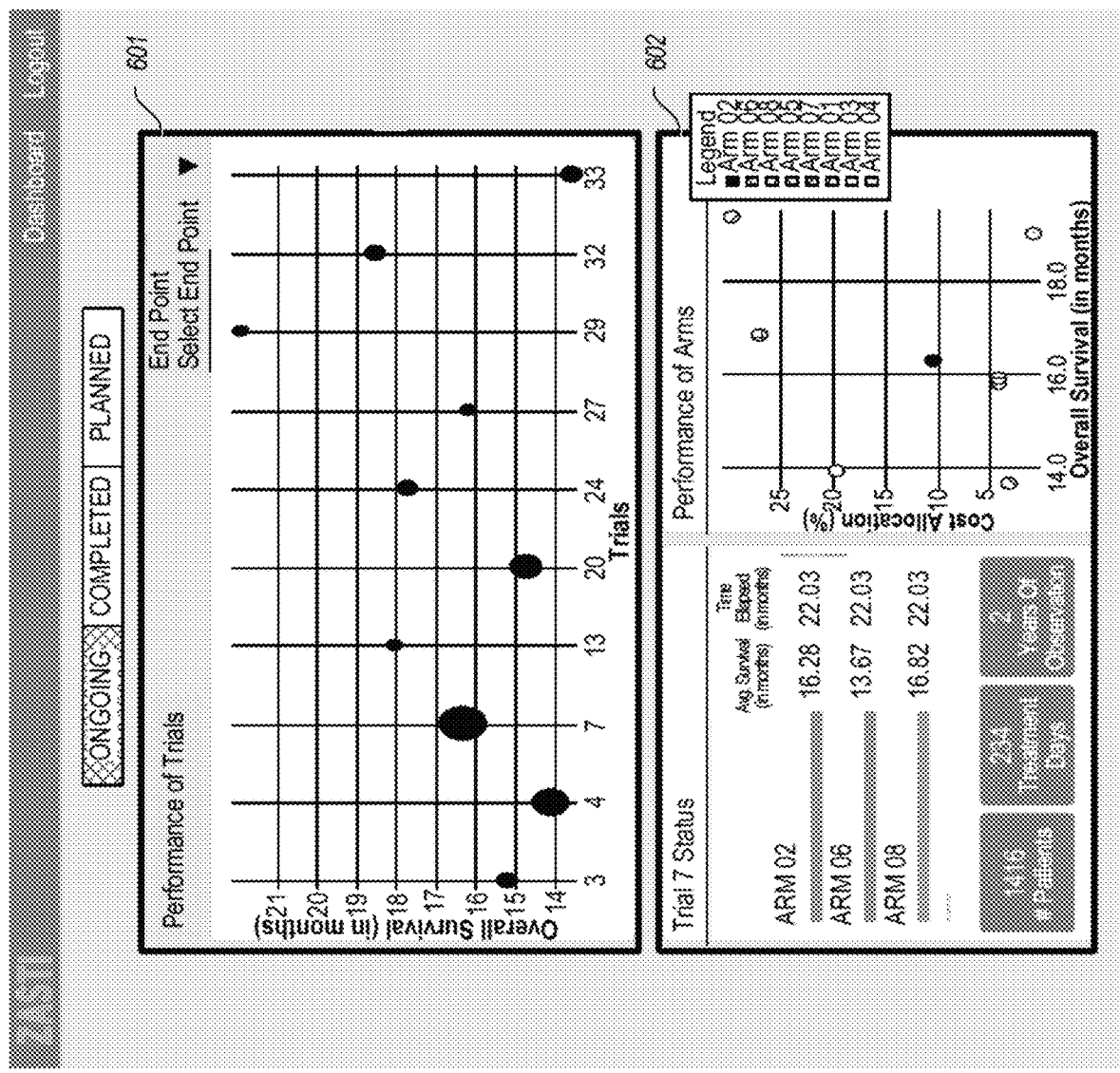
FIG. 6 is a display diagram showing a sample ongoing trials details user interface presented by the facility in some embodiments.

FIG. 6 is a display diagram showing a sample ongoing trials details user interface presented by the facility in some embodiments. The user interface 600 includes charts 601 and 602. In chart 601, the results of trials are measured in terms of overall survival rate. The size of each bubble indicates a cost allocation for that trial estimated using industry averages for each trial and phase in oncology. If the cost allocation to a trial is high and survival of a particular trial is less than average survival for all trials, then this trial may not be cost efficient. A manager can look at this and propose reallocation of the associated cost resources or just drop the trial or ARM. In chart 602, on selecting a trial, status and performance of various ARMs within the trial can be monitored here. The facility assess the performance of different ARMs as follows: red, for survival is estimated of a particular ARM<Average survival of trial, while for green, survival of a particular ARM>Average survival of trial.

Figure 7:
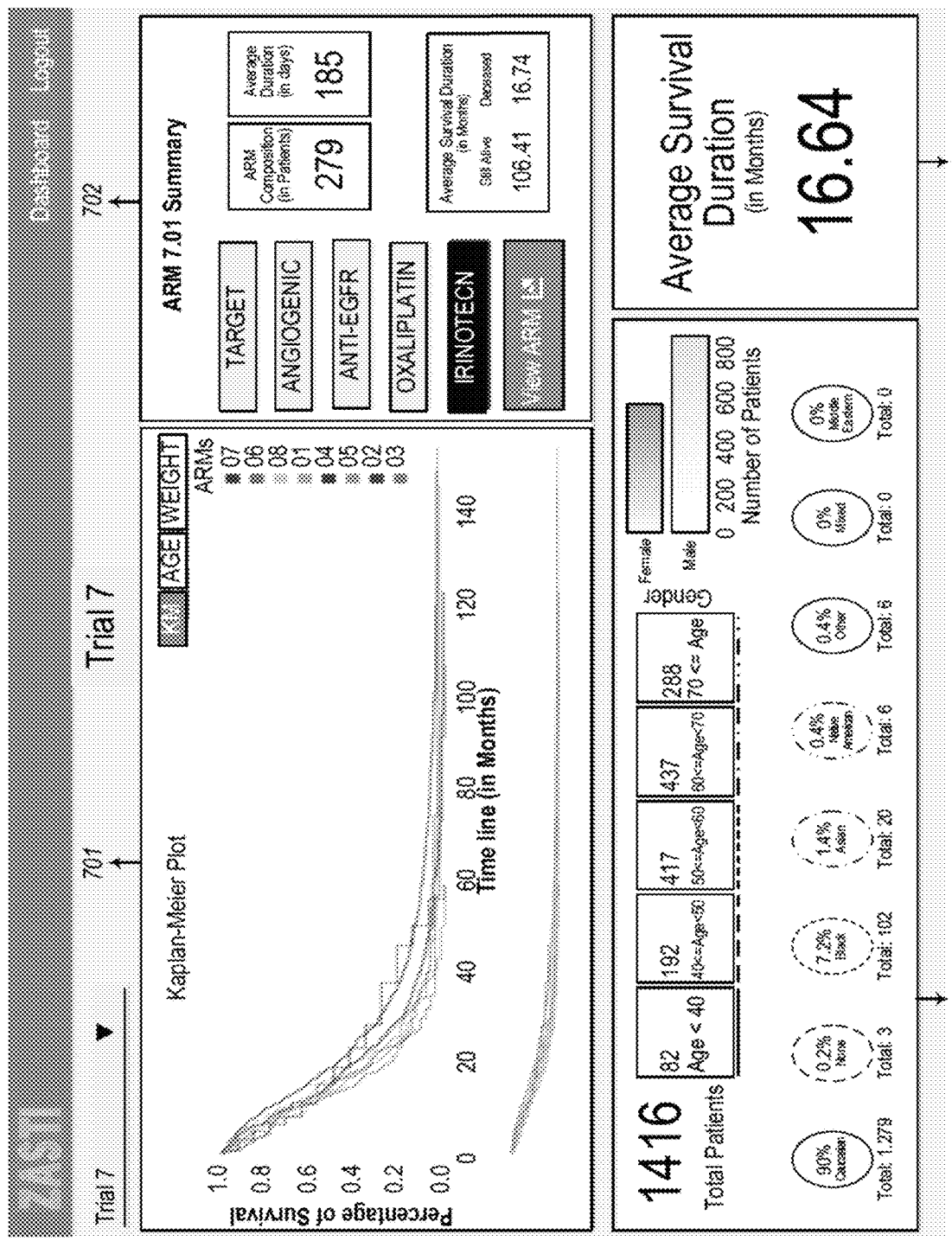
FIG. 7 is a display diagram showing a sample trial dashboard user interface presented by the facility in some embodiments.

FIG. 7 is a display diagram showing a sample trial dashboard user interface presented by the facility in some embodiments. The user interface 700 is made up of charts 701-704. Chart 701 contains Kaplan-Meier survival curves, which graphically display the time until study participants developed a particular event or endpoint, often death, or an event such as recurrence of cancer. A trial contains different ARMs corresponding to different treatments. Percentage survival for different ARMs is displayed. Chart 702 summarizes this trial's 5 treatment regimens and ARMs corresponding to combinations of these regimens is displayed. It also provides a summary of a particular ARM in the current trial and facility to drill down into further analysis of an ARM. Chart 703 shows demographics aggregates (age, gender and ethnicity distribution) for the trial. Chart 704 shows Average Survival Duration—the average survival time for the deceased and alive patients separately in this trial.

Figure 8:
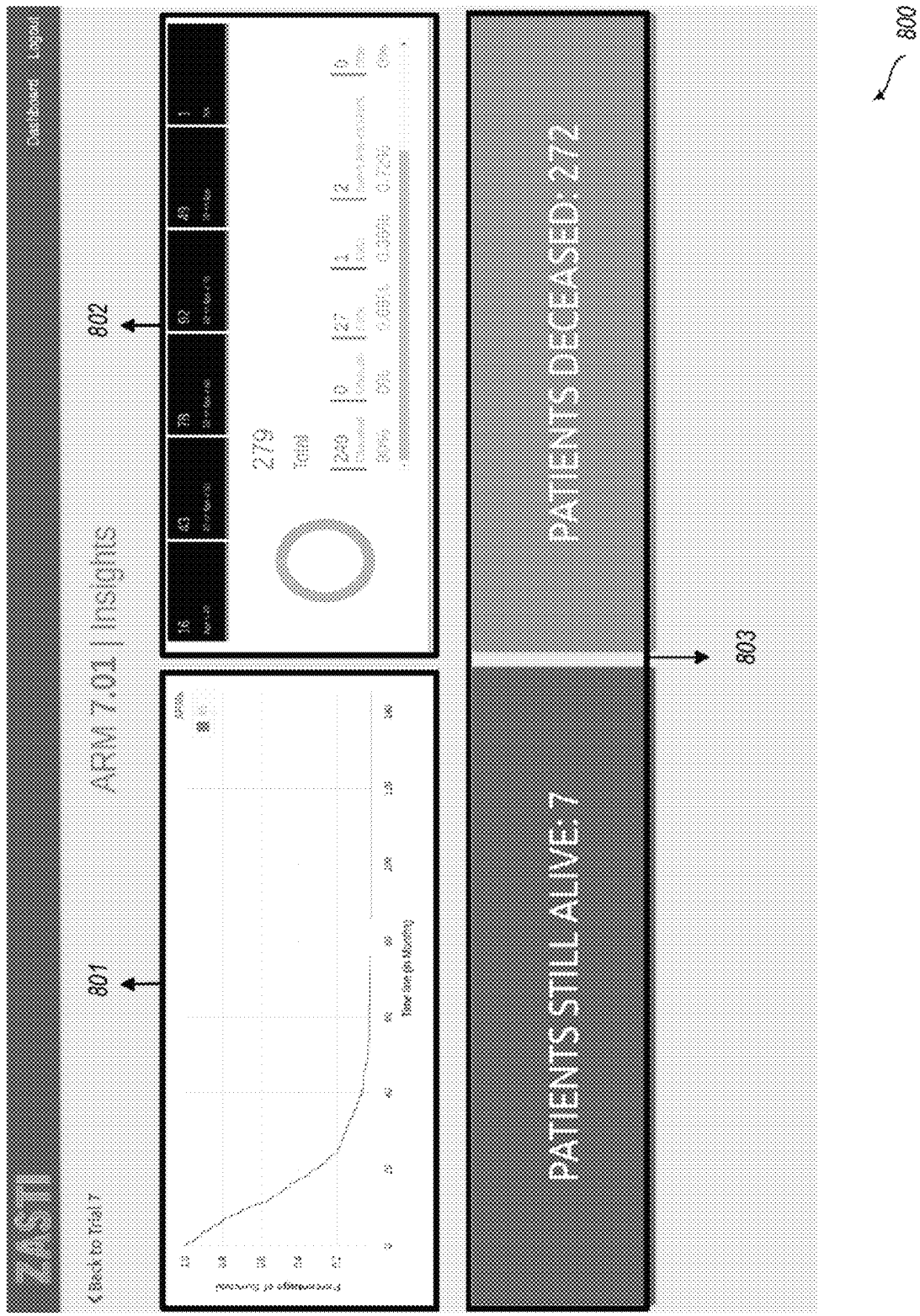
FIG. 8 is a display diagram showing a sample ARM dashboard user interface presented by the facility in some embodiments.

FIG. 8 is a display diagram showing a sample ARM dashboard user interface presented by the facility in some embodiments. The user interface 800 includes charts 801, 802, and 803, together portraying the responsiveness of patients in the ARM to treatment in accordance with the ARM. Chart 801 contains a Kaplan curve showing the progression of the ARM in terms of survival percentage versus time. Chart 802 shows demographics for the ARM, such as age, gender, and ethnicity distributions. Chart 803 shows alive and deceased patient aggregates for the ARM. The values change as the user moves forward in the ARM by hovering on the curve. Individual patient progress can be monitored.

Figure 9:
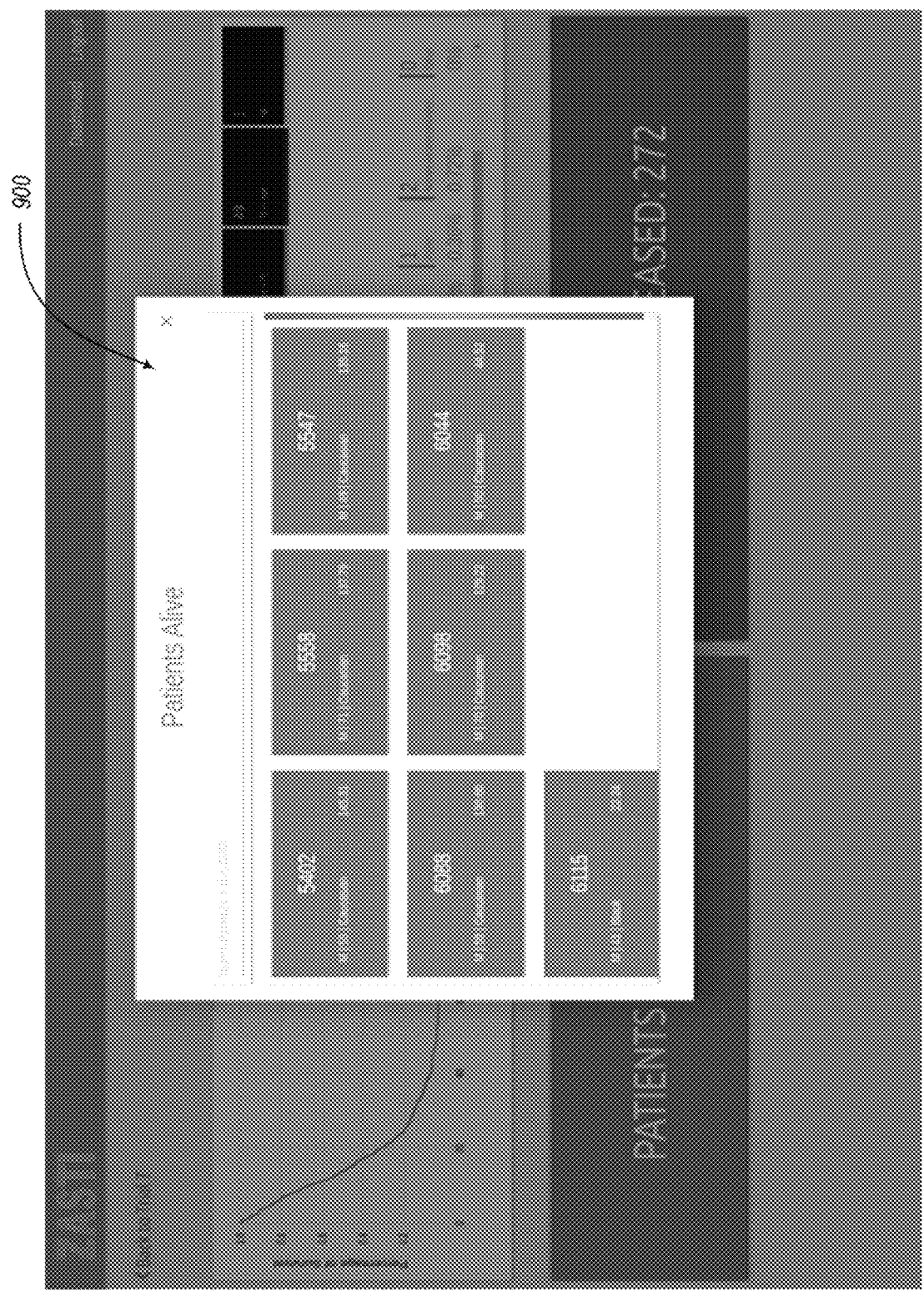
FIG. 9 is a display diagram showing a sample snapshot interface presented by the facility in some embodiments.

FIG. 9 is a display diagram showing a sample snapshot interface presented by the facility in some embodiments. The user interface 900 shows an overview of the Patients Alive or Deceased along the duration of the trial. As time passes, the number of patients who are dead changes, enabling performance of the drug can be monitored. In this case, the provided overview is of patients who are alive, selected based on the user clicking on the patients still alive aggregate shown in FIG. 8. The user can cause a similar overview to be displayed for patients deceased by clicking on this aggregate in FIG. 8. An individual patient progress report can be examined either by directly clicking on the patient card or searching for the patient id on the search bar.

Figure 10:
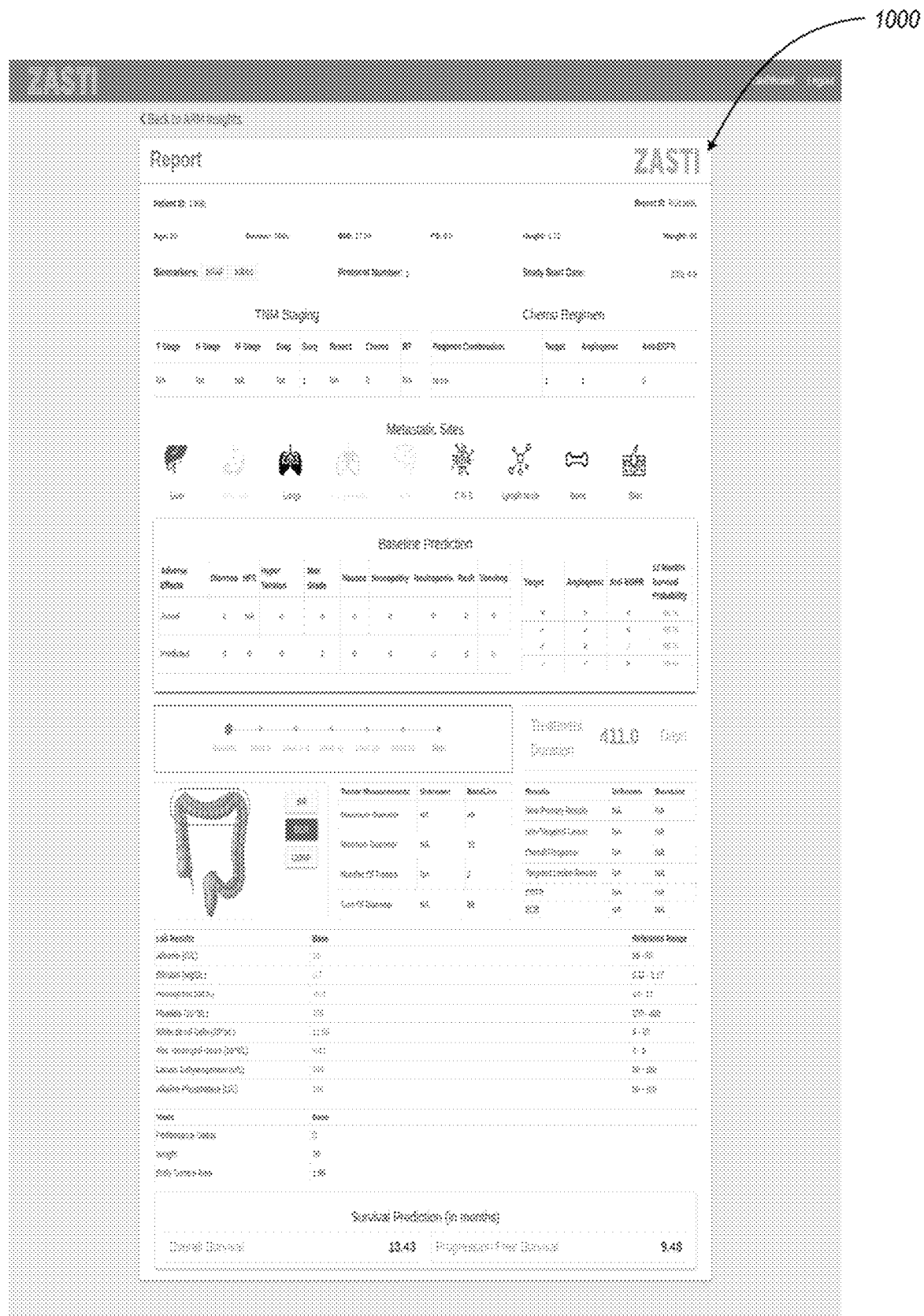
FIGS. 10-12 are display diagrams showing a sample patient test results report presented by the facility in some embodiments.
Figure 11:
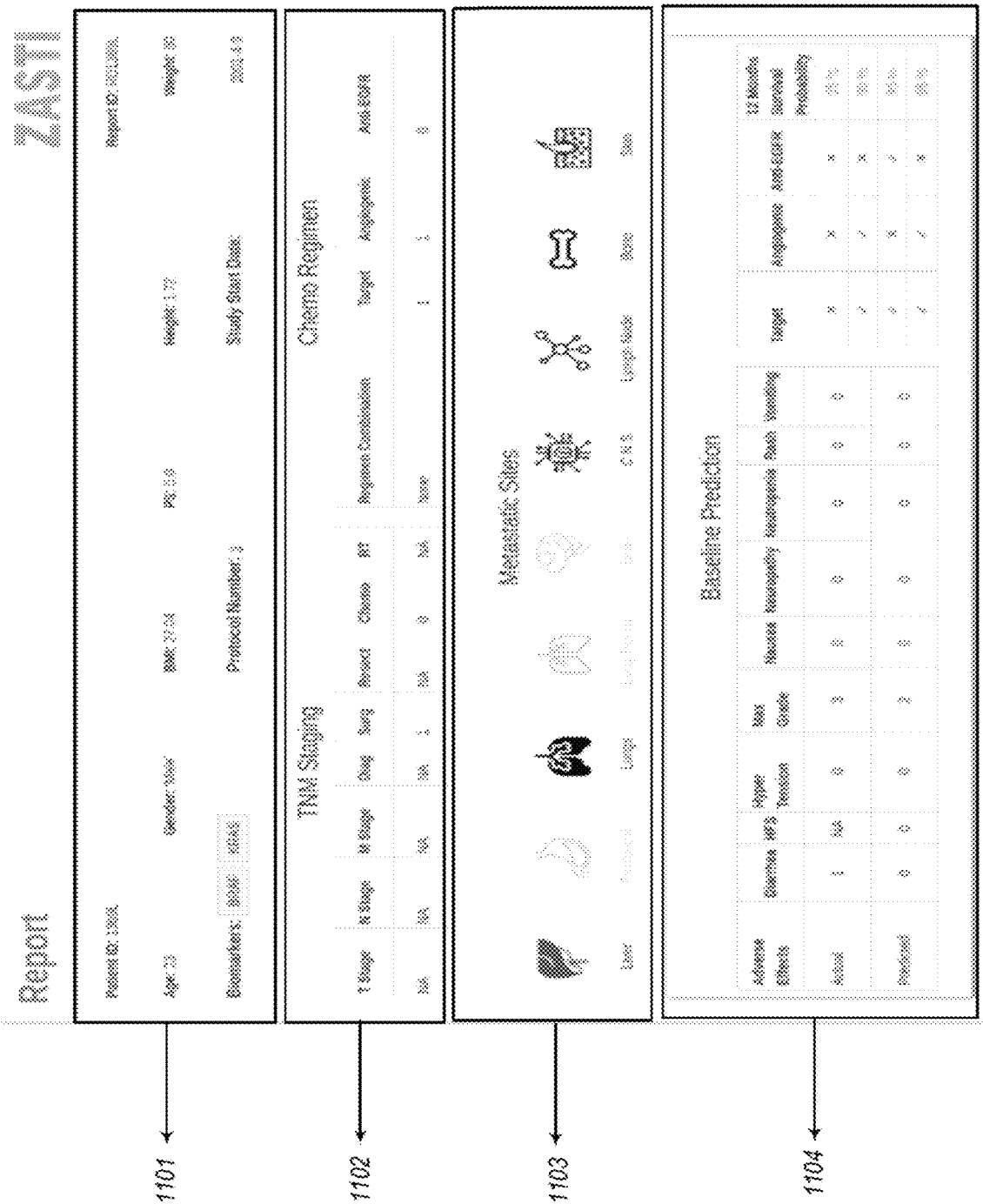
Figure 12:
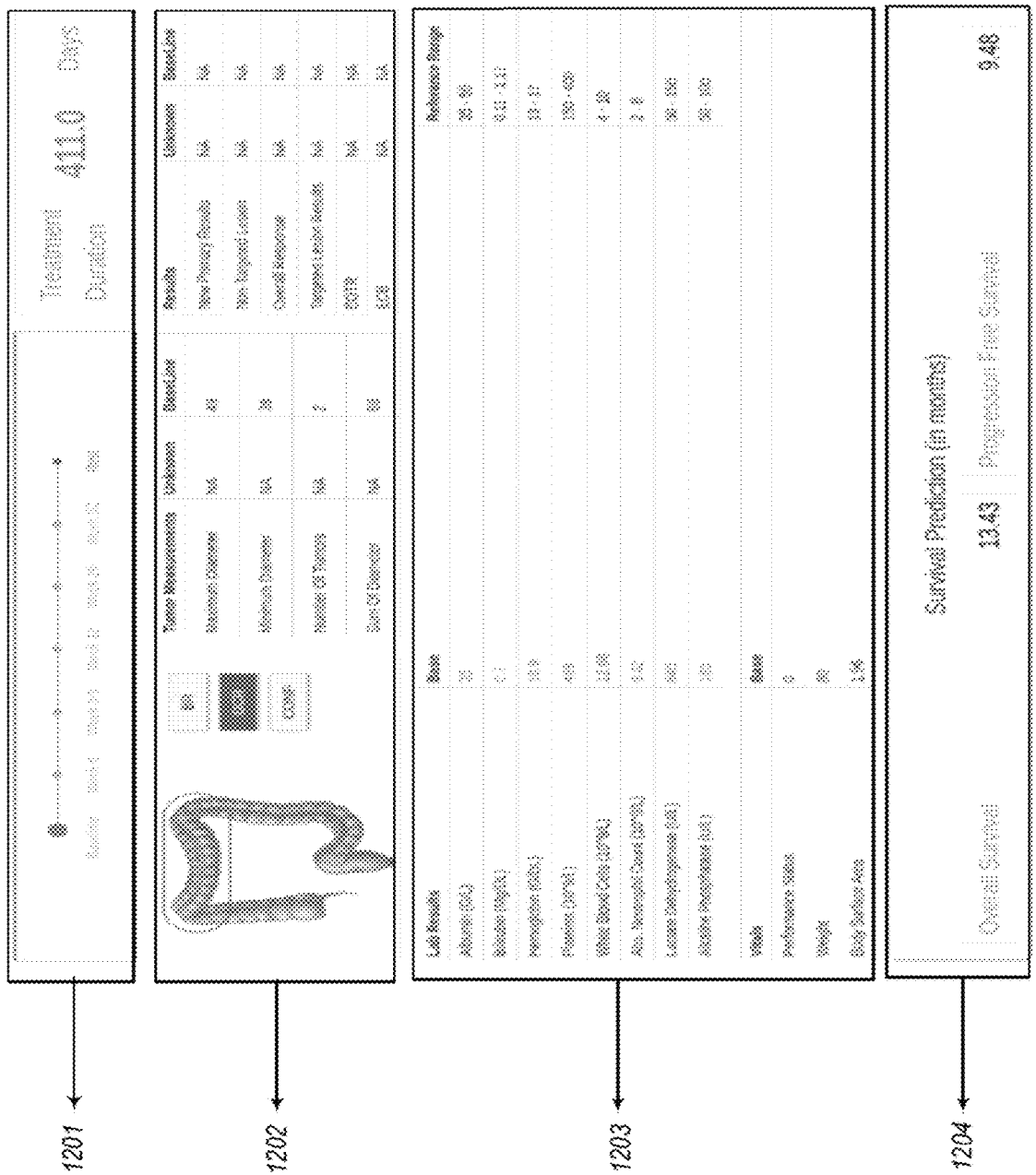

FIGS. 10-12 are display diagrams showing a sample patient test results report presented by the facility in some embodiments. The report 1000 contains various information about the patient's test results.

FIGS. 11 and 12 show the top and bottom halves of the patient test results report from FIG. 9 in greater detail.

Referring to FIG. 11, in section 1101, the report contains clinical data values for the patient—including prior treatments and tests undertaken—without identifying information. Section 1102 of the report contains a TMM classification of the patient's malignant tumors, and the patient's chemotherapy regimen or regimens. TNM Classification of Malignant Tumors is a globally recognized standard for classifying the extent of spread of cancer. A chemotherapy regimen is a regimen for chemotherapy, defining the drugs to be used, their dosage, the frequency and duration of treatments, and other considerations. Section 1103 of the report identifies the patient's Metastatic Sites: Red indicates—Site has been affected, Black—Tests have been taken, Grey—No tests taken. Section 1104 of the report contains a baseline prediction for the patient. From baseline data or at the start of the trial, the facility predicts whether or not the patient will survive after 12 months if given different treatment regimens.

Referring to FIG. 12, in section 1201, the report shows the progression of the patient over different time intervals. Section 1202 shows the primary organ that has been affected; the location of the cancer in the organ and other details about the tumor are captured here. Section 1203 evaluates the progression of patient through an ARM, i.e., all the test and lab results are represented from week 0 to week 52. Values in red indicate below normal and green indicate normal. Section 1204 shows the overall survival rate predicted for the patient. The prediction is made in terms of overall survival and progression free survival as end points. The report indicates that this patient will survive after 12 months for any combination of treatment regimen. Our prediction: 13.43 months.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method in a computing system, comprising:
   obtaining information describing one or more completed clinical trials;
   extracting features from the obtained clinical trial information;
   splitting the extracted features into a first dataset of exclusively time-series data and a second dataset of exclusively non-time-series data;
   using the first dataset of exclusively time-series data to train a time-series data model for predicting clinical outcomes;
   using the second dataset of exclusively non-time-series data to train an interpretable non-time-series data model for predicting clinical outcomes;
   obtaining information describing a subject patient;
   splitting the information describing a subject patient into time-series patient data and non-time-series patient data;
   applying the time-series data model to the time-series patient data to predict a first clinical outcome for the subject patient;
   applying the interpretable non-time-series data model to the non-time-series data to predict a second clinical outcome for the subject patient;
   generating a dashboard used to present one or more of: at least a portion of the information describing the subject patient and at least a portion of the obtained clinical trial information;
   generating a combined clinical outcome by combining the first clinical outcome with the second clinical outcome; and
   presenting the combined clinical outcome within the generated dashboard.

2. The method of claim 1 wherein predicting a clinical outcome for the subject patient comprises merging clinical outcome predictions produced by applying the trained models.

3. The method of claim 1 wherein the time-series data model comprises a recurrent neural network.

4. The method of claim 1 wherein the time-series data model comprises a long short term memory.

5. The method of claim 1 wherein the time-series data model comprises a hierarchical neural attention encoder.

6. The method of claim 1 wherein the interpretable non-time-series data model comprises a forest of gradient-boosted trees.

7. The method of claim 1, further comprising causing the predicted clinical outcome to be displayed.

8. One or more memories collectively storing a compound patient survival prediction statistical model data structure, the data structure comprising:
   a dataset of survival observations obtained from one or more cancer treatment clinical trials, the dataset of survival observations being split into time-series data and non-time-series data;
   a first submodel trained to predict patient survival using survival observations obtained from one or more cancer treatment clinical trials, the first submodel being a cyclic neural network, the first submodel exclusively utilizing the time-series data; and
   a second submodel trained to predict patient survival using survival observations obtained from one or more cancer treatment clinical trials, the second submodel being a forest of gradient-boosted trees, the second submodel exclusively utilizing the non-time-series data, such that the models represented in the data structure can be applied to information about a patient to predict survival of the patient; and
   a dashboard presenting first output generated from applying the time-series data to the first submodel, second output generated from applying the non-time-series data to the second submodel, and one or more of: clinical trial data and patient data.

9. The one or more memories of claim 8 wherein the first submodel is a recurrent neural network.

10. The one or more memories of claim 8 wherein the first submodel is a long short term memory.

11. The one or more memories of claim 8 wherein the first submodel is a hierarchical neural attention encoder.

12. One or more memories collectively having contents configured to cause a computing system to perform a method, the method comprising:
   obtaining information describing one or more completed clinical trials;

extracting features from the obtained clinical trial information;

splitting the extracted features into a first dataset of exclusively time-series data and a second dataset of exclusively non-time-series data;

using the first dataset of exclusively time-series data to train a time-series data model for predicting clinical outcomes;

using the second dataset of exclusively non-time-series data to train an interpretable non-time-series data model for predicting clinical outcomes;

obtaining information describing a subject patient;

splitting the information describing a subject patient into time-series patient data and non-time-series patient data;

applying the time-series data model to the time-series patient data to predict a first clinical outcome for the subject patient;

applying the interpretable non-time-series data model to the non-time-series data to predict a second clinical outcome for the subject patient;

generating a dashboard used to present one or more of: at least a portion of the information describing the subject patient and at least a portion of the obtained clinical trial information;

generating a combined clinical outcome by combining the first clinical outcome with the second clinical outcome; and presenting the combined clinical outcome within the generated dashboard.

13. The one or more memories of claim 12 wherein predicting a clinical outcome for the subject patient comprises merging clinical outcome predictions produced by applying the trained models.

14. The one or more memories of claim 12 wherein the time-series data model comprises a recurrent neural network.

15. The one or more memories of claim 12 wherein the time-series data model comprises a long short term memory.

16. The one or more memories of claim 12 wherein the time-series data model comprises a hierarchical neural attention encoder.

17. The one or more memories of claim 12 wherein the interpretable non-time-series data model comprises a forest of gradient-boosted trees.

18. The one or more memories of claim 12, the method further comprising causing the predicted clinical outcome to be displayed.

* * * * *